(12) United States Patent
Ng et al.

(10) Patent No.: US 10,900,091 B2
(45) Date of Patent: Jan. 26, 2021

(54) MIR-133A AS A MARKER FOR COLORECTAL CANCER

(71) Applicant: The Chinese University of Hong Kong, Hong Kong (CN)

(72) Inventors: Siu Man Simon Ng, Hong Kong (CN); Jun Yu, Hong Kong (CN); Joseph Jao Yiu Sung, Hong Kong (CN); Yujuan Dong, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 0 days.

(21) Appl. No.: 16/361,830

(22) Filed: Mar. 22, 2019

(65) Prior Publication Data

US 2020/0291479 A1    Sep. 17, 2020

Related U.S. Application Data

(60) Provisional application No. 62/819,030, filed on Mar. 15, 2019.

(51) Int. Cl.
| | |
|---|---|
| *C12Q 1/6886* | (2018.01) |
| *C12N 15/113* | (2010.01) |
| *A61K 31/282* | (2006.01) |
| *A61K 45/06* | (2006.01) |

(52) U.S. Cl.
CPC .......... *C12Q 1/6886* (2013.01); *A61K 31/282* (2013.01); *A61K 45/06* (2013.01); *C12N 15/113* (2013.01); *C12N 2310/141* (2013.01); *C12Q 2600/106* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | | |
|---|---|---|---|---|
| 9,682,095 | B2 * | 6/2017 | Berezikov | C12N 15/111 |
| 2010/0129828 | A1 * | 5/2010 | Beaulieu | G01N 33/57419 |
| | | | | 435/7.1 |
| 2013/0288258 | A1 * | 10/2013 | Galandiuk | C12Q 1/6886 |
| | | | | 435/6.12 |
| 2013/0316925 | A1 * | 11/2013 | Marsh | C12N 15/111 |
| | | | | 506/9 |
| 2014/0141986 | A1 * | 5/2014 | Spetzler | C12Q 1/6886 |
| | | | | 506/9 |

OTHER PUBLICATIONS

Dong et al. Mol Cancer Res 11 pp. 1051-1060 (Year: 2013).*
Cole, et al. "Pharmacological characterization of multidrug resistant MRP-transfected human tumor cells." Cancer research 54, No. 22 (1994): 5902-5910.
Dong, et al. "Tumor suppressor functions of miR-133a in colorectal cancer." Molecular Cancer Research 11, No. 9 (2013): 1051-1060.
Dong, et al. "MicroRNA dysregulation as a prognostic biomarker in colorectal cancer." Cancer management and research 6 (2014): 405.
Dong, et al. "MicroRNA dysregulation in colorectal cancer: a clinical perspective." British journal of cancer 104, No. 6 (2011): 893.
Godwin, et al. "High resistance to cisplatin in human ovarian cancer cell lines is associated with marked increase of glutathione synthesis." Proceedings of the National Academy of Sciences 89, No. 7 (1992): 3070-3074.
Ha, et al. "Regulation of microRNA biogenesis." Nature reviews Molecular cell biology 15, No. 8 (2014): 509.
Hall, et al. "The role of cellular accumulation in determining sensitivity to platinum-based chemotherapy." Annu. Rev. Pharmacol. Toxicol. 48 (2008): 495-535.
Higashimoto, et al. "Expression of copper-transporting P-type adenosine triphosphatase in human esophageal carcinoma." International journal of molecular medicine 11, No. 3 (2003): 337-341.
Leung, et al. "Laparoscopic resection of rectosigmoid carcinoma: prospective randomised trial." the Lancet 363, No. 9416 (2004): 1187-1192.
Meng, et al. "Comparison of microRNA deep sequencing of matched formalin-fixed paraffin-embedded and fresh frozen cancer tissues." PloS one 8, No. 5 (2013): e64393.
Miyashita, et al. "Expression of copper-transporting P-type adenosine triphosphatase (ATP7B) as a chemoresistance marker in human oral squamous cell carcinoma treated with cisplatin." Oral oncology 39, No. 2 (2003): 157-162.
Nakagawa, et al. "Expression of copper-transporting P-type adenosine triphosphatase (ATP7B) correlates with cisplatin resistance in human non-small cell lung cancer xenografts." Oncology reports 20, No. 2 (2008): 265-270.
Ng, et al. "Differential expression of microRNAs in plasma of patients with colorectal cancer: a potential marker for colorectal cancer screening." Gut 58, No. 10 (2009): 1375-1381.
Ng, et al. "Laparoscopic-assisted versus open abdominoperineal resection for low rectal cancer: a prospective randomized trial." Annals of surgical oncology 15, No. 9 (2008): 2418-2425.
Ng, et al. "laparoscopic-assisted versus open total mesorectal excision with anal sphincter preservation for mid and low rectal cancer: a prospective randomized trial: f01." Colorectal Disease 11 (2009): 2.
Ng, et al. "Long-term oncologic outcomes of laparoscopic versus open surgery for rectal cancer: a pooled analysis of 3 randomized controlled trials." Annals of surgery 259, No. 1 (2014): 139-147.
Ng, et al., Comments on MRC Classic Trial, the Lancet, vol. 366, Aug. 27, 2005, 713.

(Continued)

*Primary Examiner* — Brian Whiteman
(74) *Attorney, Agent, or Firm* — Kilpatrick Townsend & Stockton LLP

(57) ABSTRACT

The present invention provides methods for assessing the likelihood of effectiveness of chemotherapy such as oxaliplatin treatment in colorectal cancer patients as well as their survival prospect by determining the level of miR-133a in the cancer tissue. A kit useful for such methods are also provided.

12 Claims, 5 Drawing Sheets
Specification includes a Sequence Listing.

(56) References Cited

OTHER PUBLICATIONS

Ohbu, et al. "Copper-transporting P-type adenosine triphosphatase (ATP7B) is expressed in human gastric carcinoma." Cancer letters 189, No. 1 (2003): 33-38.

Peskoe, et al. "Differential long-term stability of microRNAs and RNU6B snRNA in 12-20 year old archived formalin-fixed paraffin-embedded specimens." BMC cancer 17, No. 1 (2017): 32.

Shields, et al. "Treatment of advanced colorectal carcinoma with oxaliplatin and capecitabine: a phase II trial." Cancer 100, No. 3 (2004): 531-537.

Sung, et al. "An updated Asia Pacific Consensus Recommendations on colorectal cancer screening." Gut 64, No. 1 (2015): 121-132.

Therasse, et al. "New guidelines to evaluate the response to treatment in solid tumors." Journal of the National Cancer Institute 92, No. 3 (2000): 205-216.

Torre, et al. "Global cancer statistics, 2012." CA: a cancer journal for clinicians 65, No. 2 (2015): 87-108.

Venook, Alan. "Critical evaluation of current treatments in metastatic colorectal cancer." the Oncologist 10, No. 4 (2005): 250-261.

Wong, et al. "Clinical significance of CDX2-positive circulating tumour cells in colorectal cancer patients." British journal of cancer 104, No. 6 (2011): 1000.

Wu, et al. "Identification of microRNA-135b in stool as a potential noninvasive biomarker for colorectal cancer and adenoma." Clinical cancer research 20, No. 11 (2014): 2994-3002.

Wu, et al. "Detection of miR-92a and miR-21 in stool samples as potential screening biomarkers for colorectal cancer and polyps." Gut 61, No. 5 (2012): 739-745.

Xi, et al. "Systematic analysis of microRNA expression of RNA extracted from fresh frozen and formalin-fixed paraffin-embedded samples." Rna 13, No. 10 (2007): 1668-1674.

\* cited by examiner

FIGURE 1A
FIGURE 1B
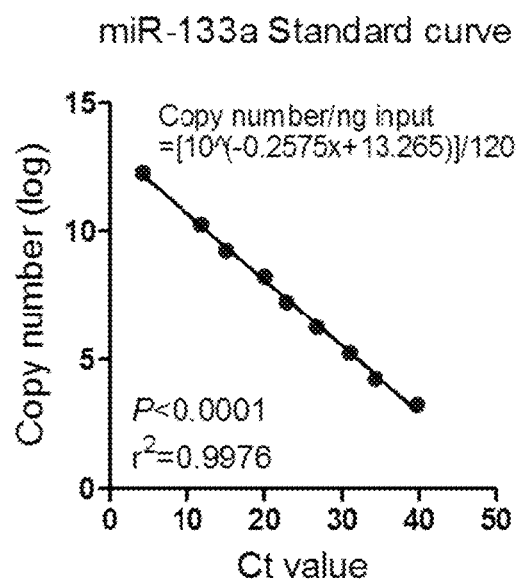
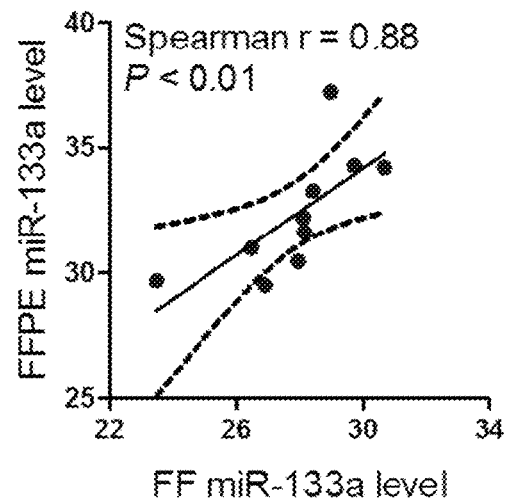

FIGURE 5A
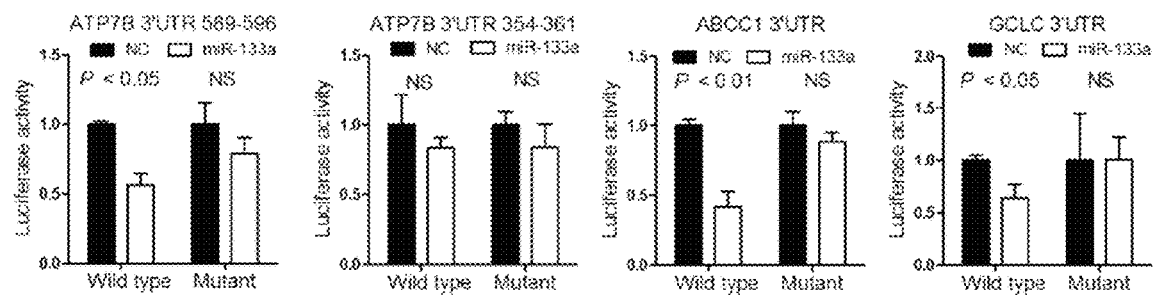
FIGURE 5B
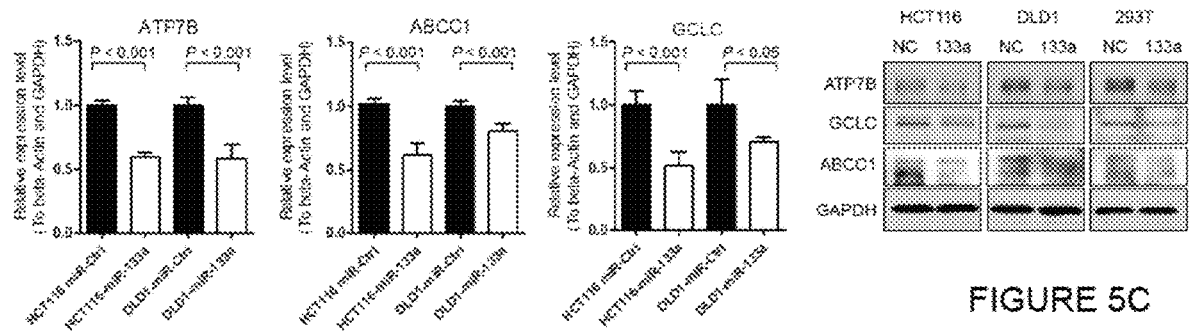
FIGURE 5C

MIR-133A AS A MARKER FOR COLORECTAL CANCER

CROSS-REFERENCES TO RELATED APPLICATIONS

This application claims the benefit of U.S. Provisional Application No. 62/819,030, filed Mar. 15, 2019, the disclosure of which is incorporated herein.

REFERENCE TO SUBMISSION OF A SEQUENCE LISTING AS A TEXT FILE

The Sequence Listing written in file080015-1132153-026710US_SL.txt created on Feb. 17, 2020, 8,192 bytes, machine format IBM-PC, MS-Windows operating system, is hereby incorporated by reference in its entirety for all purposes.

BACKGROUND OF THE INVENTION

Colorectal cancer (CRC) is the third most common cancer and the third leading cause of cancer mortality worldwide (1). Both the incidence and death rate of CRC are increasing rapidly and maintaining an upward trend in Asian countries (2). While surgery still remains the mainstay of curative treatment for CRC, most patients with advanced/metastatic disease will require chemotherapy as a palliative treatment to hopefully prolong survival. Oxaliplatin, a third generation diaminocyclohexane-containing platinum compound that inhibits DNA synthesis and prevents DNA transcription, has had a significant impact on treatment strategies for patients with metastatic CRC (mCRC). Unfortunately, a significant proportion of patients fail to respond to such treatments, and some may even experience worse outcomes as a result of drug-induced toxicities. Genetic background of an individual can influence response to anti-cancer therapy. It is therefore imperative to identify predictive molecular markers that can help select those patients who may benefit from oxaliplatin-based chemotherapy.

Archival formalin-fixed paraffin-embedded (FFPE) tissues have been an invaluable resource for cancer biomarker identification. FFPE samples provide a historical record of tissue histology, protein and nucleic acid expression that can be correlated with long-term follow up of disease outcomes. Recently, comparative analyses of FFPE and frozen tissues revealed a positive correlation in miRNAs expression, suggesting that miRNAs are unusually stable when compared to longer mRNA transcripts, probably due to their small size and secondary structure (3, 4). Because of their stability in FFPE tissue, miRNAs from FFPE samples therefore has the potential to serve as invaluable cancer biomarkers. miRNAs belong to a class of highly conserved ~22-nucleotides single-stranded RNAs that suppress target genes translation or induce messenger RNA (mRNA) degradation through binding to the 3' untranslation region (3'UTR) (5). By targeting multiple transcripts, miRNAs epigenetically regulate fundamental cellular processes as well as cancer development and progression. While their previous study indicates that hsa-miR-133a-3p (miR-133a, MIMAT0000427) sensitizes CRC cells to oxaliplatin induced apoptosis (6), in this study, the present inventors have designed a set of primers to detect the miR-133a expression and has therefore devised a method to predict mCRC patient response to oxaliplatin treatment and prognosis.

BRIEF SUMMARY OF THE INVENTION

The present inventors have discovered the important correlation between miR-133a expression level in colon cancer tissue and a patient's likelihood to benefit from chemotherapy such as oxaliplatin treatment, as well as the important correlation between miR-133a expression level in colon cancer tissue and a patient's mortality rate from this disease.

As such, in the first aspect, the present invention provides a method for determining treatment plan in a colorectal cancer patient. The method includes these steps: (a) measuring miR-133a level in a colorectal cancer sample taken from the patient; (b) comparing the level obtained in step (a) with a cut-off value; and (c) determining chemotherapy such as oxaliplatin treatment as likely effective to the patient when the level obtained in step (a) is higher than the cut-off value, and providing to the patient the chemotherapy such as oxaliplatin treatment; or determining the chemotherapy such as oxaliplatin treatment as likely ineffective to the patient when the level obtained in step (a) is no higher than the cut-off value, and providing to the patient an alternative treatment different from the chemotherapy (such as oxaliplatin treatment).

In some embodiments, the colorectal cancer patient has stage IV colorectal cancer including colorectal cancer with distant metastasis. In some embodiments, step (a) comprises a polymerase chain reaction (PCR) for measuring the miR-133a level. In some embodiments, the PCR is a reverse transcription polymerase chain reaction (RT-PCR). In some embodiments, the PCR is a quantitative polymerase chain reaction (qPCR). In some embodiments, a primer set comprising SEQ ID NO:1, 2, 3 or 4 is used in the RT-PCR and qPCR. In some embodiments and depending on the sample type used, the cut-off value is about 1000, 1100, 1200, 1300, 1400, 1500, 1550, 1600, 1650, 1700, 1750, 1800, 1850, 1900, 1950, 2000, 2050, 2100, 2150, 2200, 2250, 2300, 2400, 2500, 2600, 2700, 2800, 2900, 3000, 4000, 5000, 6000, 7000, 8000, 9000, 10000, 11000, 12000, 13000, 14000, or 15000 copy number per µg input, e.g., about 1933 copy number per µg input of formalin-fixed paraffin-embedded (FFPE) sample or about 11,312 copy number per µg input of frozen tissue (FF) sample. In some embodiments, when two colorectal cancer patients are tested using this method for their miR-133a level, the first patient having a higher miR-133a level is deemed to have a higher possibility of having a successful therapeutic outcome from oxaliplatin treatment compared to the second patient having a lower miR-133a level. In some embodiments, the first patient's miR-133a level is above the cut-off value. In some embodiments, the method further comprises in step (c), when the level obtained in step (a) is no higher than the cut-off value, (i) providing to the patient a therapy causing increased miR-133a level in the patient's colorectal tissue; and (ii) providing to the patient the chemotherapy, such as oxaliplatin treatment. In some embodiments, the method further comprises in step (c), when the level obtained in step (a) is no higher than the cut-off value, providing to the patient an alternative treatment different from the oxaliplatin based chemotherapy. In some embodiments, the therapy comprises administering to the patient an expression cassette directing expression of miR-133a. In some embodiments, the expression cassette is a part of a viral vector or viral particle.

In a second aspect, the present invention provides a method for assessing likelihood of mortality caused by colorectal cancer among colorectal cancer patients. The method comprises these steps: (a) measuring miR-133a level in a first colorectal cancer sample taken from a first patient and in a second colorectal cancer sample taken from a second patient; (b) determining the miR-133a level in the first sample as being higher than the miR-133a level in the second sample; and (c) determining the second patient as having a higher likelihood of mortality caused by colorectal cancer than the first patient.

In some embodiments, each of the first and second patients has stage IV colorectal cancer. In some embodiments, step (a) comprises a polymerase chain reaction (PCR). In some embodiments, the PCR is a reverse transcription polymerase chain reaction (RT-PCR) and quantitative PCR (qPCR). In some embodiments, a primer set comprising SEQ ID NO:1, 2, 3 or 4 is used in the RT-PCR and qPCR. In some embodiments, the likelihood of mortality is in regard to a subsequent time period of about 1, 2, 3, 4, or 5 years or about 10, 20, 30, 40, or 50 months.

In a third aspect, the present invention provides a method for enhancing chemotherapy in a colorectal cancer patient. The method includes the step of administering to the patient an effective amount of an inhibitor of at least one of ATPase Cu$^{++}$ transporting beta polypeptide (ATP7B), ATP-binding cassette sub-family C member 1 (ABCC1), and γ-glutamylcysteine ligase (GCLC) just prior to or concurrently with chemotherapy. In some embodiments, the inhibitor is administered prior to concurrently with oxaliplatin. In some embodiments, the inhibitor is miR-133a, an expression cassette directing expression of miR-133a, or a viral vector comprising the expression cassette.

In a fourth aspect, the present invention provides a kit for treating colorectal cancer, comprising (1) a first container containing an RT-PCR reagent for measuring miR-133a level in a colorectal cancer sample taken from a colorectal cancer patient; and (2) a second container containing a composition comprising an effective amount of a chemotherapeutic agent such as oxaliplatin. In some embodiments, the kit further comprises a third container containing a composition comprising an effective amount of at least one inhibitor of ATPase Cu$^{++}$ transporting beta polypeptide (ATP7B), ATP-binding cassette sub-family C member 1 (ABCC1), or γ-glutamylcysteine ligase (GCLC). In some embodiments, the inhibitor is miR-133a, an expression cassette directing expression of miR-133a, or a viral vector comprising the expression cassette. In some embodiments, the kit further comprises an instruction manual.

BRIEF DESCRIPTION OF THE DRAWINGS

FIG. 1A-1B: shows the performance of self-designed miR-133a primer set and consistency of miR-133a expression in CRC FFPE and FF samples in an embodiment. (FIG. 1A) miR-133a standard curve was generated by qPCR using the self-designed miR-133a primer set. (FIG. 1B) The expression level of tissue miR-133a in FFPE samples was positively correlated with its expression in matched FF samples.

(FIG. 2A) miR-133a expression level in CRC tissues and paired adjacent normal tissues was analyzed by qPCR. (FIG. 2B) The expression level of miR-133a in CRC tissues and paired adjacent normal tissues (FFPE samples) from oxaliplatin responder and non-responder groups was analyzed by qPCR.

(FIG. 3A) Receiver operating characteristics (ROC) curves based on using miR-133a was plotted to discriminate oxaliplatin responder and non-responder CRC patients. MiR-133a yields an area under the curve (AUC) value of 0.73.

(FIG. 3B) and (FIG. 3C) CRC patients with lower tissue miR-133a expression had a poor overall survival and progress-free survival. (FIG. 3D) CRC patients in the validation cohort with lower tissue miR-133a expression had a poor overall survival.

FIGS. 5A-5C: shows miR-133a sensitizes CRC cells to oxaliplatin treatment through suppressing ATP7B, ABCC1, and GCLC in an embodiment. (FIG. 5A) miR-133a targeted the wild-type but not the mutant 3'UTR of ATP7B, ABCC1 and GCLC. (FIG. 5B) miR-133a decreased the ATP7B, ABCC1 and GCLC mRNA level in HCT116 and DLD1 cells as determined by qPCR. (FIG. 5C) miR-133a decreased the ATP7B, ABCC1 and GCLC protein level in HCT116, DLD1 and 293T cells, as determined by western blot.

DEFINITIONS

Figure 2A:
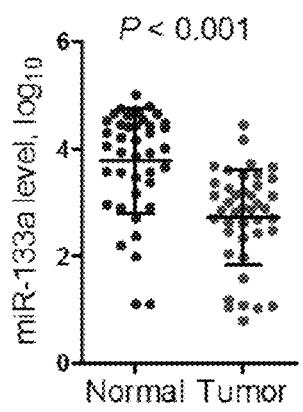
FIGS. 2A-2B: shows miR-133a expression was significantly lower in the tumor tissues from non-responder groups compared with those with good response in an embodiment.

In this disclosure the terms "colorectal cancer (CRC)" and "colon cancer" have the same meaning and refer to a cancer of the large intestine (colon), the lower part of human digestive system, although rectal cancer often more specifically refers to a cancer of the last several inches of the colon, the rectum. A "colorectal cancer cell" is a colon epithelial cell possessing characteristics of colon cancer and encompasses a precancerous cell, which is in the early stages of conversion to a cancer cell or which is predisposed for conversion to a cancer cell. Such cells may exhibit one or more phenotypic traits characteristic of the cancerous cells.

"Oxaliplatin" is a cancer drug also known under the brand new Eloxatin. It's chemical structure is:

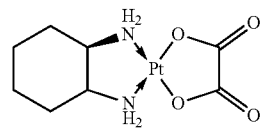

Often used as the first line of therapy in treating metastatic colorectal cancer, Oxaliplatin is typically administered to patients by intravenous injection.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in WO01/12654, which may improve the stability (e.g., half-life), bioavailability, and other characteristics of a polypeptide comprising one or more of such D-amino acids. In some cases, one or more, and potentially all of the amino acids of a therapeutic polypeptide have D-chirality.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used herein, the term "gene expression" is used to refer to the transcription of a DNA to form an RNA molecule encoding a particular protein or the translation of a protein encoded by a polynucleotide sequence. In other words, both mRNA level and protein level encoded by a gene of interest are encompassed by the term "gene expression level" in this disclosure.

An "expression cassette" is a nucleic acid construct, generated recombinantly or synthetically, with a series of specified nucleic acid elements that permit transcription of a particular polynucleotide sequence in a host cell, for example, the transcription of a microRNA such as miR-133a. An expression cassette may be part of a plasmid, viral genome, or nucleic acid fragment. In other words, an expression cassette may be transferred or delivered as a part or/in the form of a bacterial plasmid or a viral vector or virus-like particle. Typically, an expression cassette includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. Other elements that may be present in an expression cassette include those that enhance transcription (e.g., enhancers) and terminate transcription (e.g., terminators), as well as those that confer certain binding affinity or antigenicity to the recombinant protein produced from the expression cassette.

As used in this application, an "increase" or a "decrease" refers to a detectable positive or negative change in quantity from a comparison control, e.g., an established standard control or cut-off value. An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, or even less variation from the standard control.

The term "inhibiting" or "inhibition," as used herein, refers to any detectable negative effect on a target biological process, such as RNA transcription, protein expression, cell proliferation, cellular signal transduction, cell proliferation, tumorigenicity, metastatic potential, and recurrence of a disease/condition. Typically, an inhibition is reflected in a decrease of at least 10%, 20%, 30%, 40%, or 50% in target process (e.g., level of a pertinent protein such as ATP7B, ABCC1, and GCLC) upon application of an inhibitor, when compared to a control where the inhibitor is not applied.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the sequence of a pertinent miRNA species. For example, "primers" can be used in a reverse-transcription polymerase chain reaction (RT-PCR) and quantitative polymerase chain reaction (qPCR) to quantify the gene expression. Typically at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. The primers used in particular embodiments are shown in Table 1 of the disclosure where their specific applications are indicated. In this disclosure the term "primer pair" means a pair of primers that hybridize to opposite strands a target DNA molecule or to regions of the target DNA which flank a nucleotide sequence to be amplified. In this disclosure the term "primer site", means the area of the target DNA or other nucleic acid to which a primer hybridizes.

The term "cut-off value," as used in the context of assessing whether a colorectal cancer patient has an elevated or depressed level of miR-133a in the colorectal cancer tissue for the purpose of determining whether the patient is a good candidate for oxaliplatin treatment, in other words, whether the patient is likely to achieve clinical improvement upon receiving oxaliplatin treatment, refers to a pre-determined value in the amount or concentration of miR-133a in a specific sample type (such as colorectal cancer tissue) processed by a specific method (such as quantitative PCR that allows for a reasonably reliable determination (for example, both sensitivity and specificity reaching at about 70%, 75%, or 80%) of the likelihood of effective oxaliplatin treatment. A cut-off value is established by analyzing the level of miR-133a among a group comprising a sufficient number (e.g., at least 8, 10, 12, 15, or 20) of colorectal cancer patients. In addition, the selected group of patients generally have a similar age (e.g., above 50, or between 50-65, or between 50-75) and a similar disease stage (e.g., stage IV) to that of a subject whose miR-133a level is assessed for indication of likelihood of responsiveness to oxaliplatin treatment. Moreover, other factors such as gender, ethnicity, and medical history are also considered and preferably closely matching between the profiles of the test subject and the selected group of individuals establishing the "cut-off value."

The term "amount" as used in this application refers to the quantity of a polynucleotide of interest or a polypeptide of interest, e.g., miR-133a, present in a sample. Such quantity may be expressed in the absolute terms, i.e., the total quantity of the polynucleotide or polypeptide in the sample, or in the relative terms, i.e., the concentration of the polynucleotide or polypeptide in the sample.

The term "treat" or "treating," as used in this application, describes to an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "effective amount" as used herein refers to an amount of a given substance that is sufficient in quantity to produce a desired effect. For example, an effective amount of an polynucleotide encoding an miRNA such as miR-133a is the amount of said polynucleotide to achieve an increased level of miR-133a in a patient's colorectal tissue, especially colorectal cancer tissue, such that the cancer cells are sensitized and more susceptible to subsequent treatment regimen including oxalipaltin administration. An amount adequate to accomplish this is defined as the "therapeutically effective dose." The dosing range varies with the nature of the therapeutic agent being administered and other factors such as the route of administration and the severity of a patient's condition.

The term "subject" or "subject in need of treatment," as used herein, includes individuals who seek medical attention due to risk of, or actual suffering from, colon cancer. Subjects also include individuals currently undergoing therapy or about to start therapy that seek information useful for making a choice or manipulation of the therapeutic regimen. Subjects or individuals in need of treatment include those that demonstrate symptoms of colon cancer or are at risk of suffering from colon cancer or its symptoms. For example, a subject in need of treatment includes individuals with a genetic predisposition or family history for colon cancer, those that have suffered relevant symptoms in the past, those that have been exposed to a triggering substance or event, as well as those suffering from chronic or acute symptoms of the condition. A "subject in need of treatment" may be any gender and at any age of life. In some cases, the subject may be a patient who has been diagnosed with advanced colorectal cancer (at least stage IV or even more advanced, e.g., with established distant metastasis).

"Inhibitors," "activators," and "modulators" of a protein (such as ATPase $Cu^{++}$ transporting beta polypeptide or ATP7B, ATP-binding cassette sub-family C member 1 or ABCC1, and γ-glutamylcysteine ligase or GCLC) refer to inhibitory, activating, or modulating molecules, respectively, identified using in vitro and in vivo assays for their capability to positively or negatively modulate a protein's expression and/or activity or to otherwise alter the expression and/or activity of the protein. The term "modulator" includes inhibitors and activators. Inhibitors are agents that, e.g., partially or totally block binding, decrease, prevent, delay activation, inactivate, desensitize, or down regulate the level or amount of the pertinent protein, potentially by suppressing downstream effects such as the growth or survival of the colorectal cancer cells. In some cases, the inhibitor directly or indirectly binds to a target DNA or RNA, such as an antisense molecule or micro RNA. Inhibitors, as used herein, are synonymous with inactivators and antagonists. Activators are agents that, e.g., stimulate, increase, facilitate, enhance activation, sensitize or up regulate the level or amount of a pertinent protein, potentially by promoting downstream effects such as the growth or survival of the colorectal cancer cells. Inhibitors, activators, and modulators can be macromolecules such as polynucleotides, polypeptides including antibodies and antibody fragments, or they can be small molecules including carbohydrate-containing molecules, siRNAs, RNA aptamers, and the like.

As used herein, the term "about" denotes a range of value encompassing +/−10% of a pre-determined value. For instance, "about 10" means 9 to 11.

In this disclosure the term "or" is generally employed in its sense including "and/or" unless the content clearly dictates otherwise.

DETAILED DESCRIPTION OF THE INVENTION

I. Introduction

The subject matter disclosed generally relates to methods for detecting miR-133a in colorectal cancer and markers for predictive response of metastatic colorectal cancer patients receiving oxaliplatin-based chemotherapy and patients outcome. The invention discloses a predictive and prognostic biomarker, miR-133a, and subsequently a method used for predictive of patients with metastatic colorectal cancer receiving oxaliplatin-based chemotherapy and prognosis of colorectal cancer survival. The present invention also provides miR-133a expression detection methods through real-time polymerase chain reaction (PCR) experiment, including the following steps: the total RNA extraction, design miR-133a specific primers; miR-133a reverse transcription; miR-133a real-time PCR quantification. The present invention uses miR-133a as a biomarker of colorectal cancer prognosis and provides a miR-133a detection method, which can detect whether stage IV colorectal cancer patients with a good response to oxaliplatin-based chemotherapy and a sound survival prospect.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

The sequence of interest used in this invention, e.g., the polynucleotide sequence of a microRNA, and synthetic oligonucleotides (e.g., primers) can be verified using, e.g., the chain termination method for double-stranded templates of Wallace et al., *Gene* 16: 21-26 (1981).

III. Acquisition of Samples and Analysis of miRNA

The present invention relates to measuring the level or amount of a specific miRNA found in a sample taken from a patient being tested, for example, a colorectal cancer sample, as a means to determine the likelihood of effective oxaliplatin treatment and the likelihood of mortality from colon cancer (or the prospect of survival) after a diagnosis of colorectal cancer is made. Thus, the first steps of practicing this invention are to obtain a sample such as a colon cancer sample from a test subject and extract RNA from the sample.

A. Acquisition and Preparation of Samples

A colorectal cancer sample is obtained from a person to be tested or monitored for treatment effectiveness or survival. Collection of such samples is typically performed by way of surgical resection or biopsy. After being obtained, the samples may be stored according to standard procedures prior to further preparation. Sample type includes frozen tissue (FF) samples and formalin-fixed paraffin-embedded (FFPE) samples. The analysis of miRNA found in a patient's colorectal cancer sample according to the present invention may be performed using established techniques. The methods for preparing tissue samples for nucleic acid extraction are well-known among those of skill in the art and described herein.

B. Extraction and Quantitation of RNA

Methods for extracting RNA from a biological sample are well-known and routinely practiced in the art of molecular biology (e.g., described by Sambrook and Russell, *Molecular Cloning: A Laboratory Manual* 3d ed., 2001). The general methods of RNA preparation can be followed, see, e.g., Sambrook and Russell, supra; various commercially available reagents or kits, such as Trizol reagent (Invitrogen, Carlsbad, Calif.), RNeasy Mini Kits (Qiagen, Hilden, Germany), miRNeasy FFPE Kit (Qiagen, Hilden, Germany) and PolyATtract® Series 9600™ (Promega, Madison, Wis.), may also be used to obtain mRNA from a biological sample from a test subject. Combinations of more than one of these methods may also be used. It is essential that all contaminating DNA be eliminated from the RNA preparations. Thus, careful handling of the samples, thorough treatment with DNase, and proper negative controls in the amplification and quantification steps should be used.

Once mRNA is extracted from a sample, the amount of any particular microRNA species, such as miR-133a, may be quantified. The preferred method for determining the miRNA level is an amplification-based method, e.g., by polymerase chain reaction (PCR), including reverse transcription-polymerase chain reaction (RT-PCR) and quantitative polymerase chain reaction (qPCR) for RNA quantitative analysis.

Prior to amplification, miRNA must be first reverse transcribed: a DNA copy (cDNA) of the target RNA must be synthesized. This is achieved by reverse transcription, which can be carried out using a specific miR-133a reverse transcription primer in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

The general methods of PCR are well-known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

IV. Establishing a Cut-Off Value

In order to establish a cut-off value for practicing the method of this invention, a group of colorectal cancer patients, especially in a pre-selected stage of the disease, e.g., stage IV is first selected. Their miR-133a level is first measured, and their responsiveness to oxaliplatin treatment is then recorded. These individuals are within the appropriate parameters, if applicable, for the purpose of assessing the likelihood of effective oxaliplatin treatment and survival prospect among colon cancer patients using the methods of the present invention. Optionally, the individuals are of matched gender, similar age, similar ethnic background, and similar medical history/family background.

The health status, including their responsiveness to oxaliplatin treatment, of the selected individuals is confirmed by well established, routinely employed methods including but not limited to general as well as specialized physical or medical examination of the individuals and general review of their medical history.

Furthermore, the selected group of patients must be of a reasonable size, such that the pertinent miRNA (e.g., miR-133a) level in the colon cancer sample obtained from the group would allow the establishment of a correlation between miR-133a level and effectiveness of oxaliplatin treatment, which would then allow the establishment of a cut-off value that reflects a reasonable prediction of whether or not an individual colorectal cancer patient would likely benefit from oxaliplatin administration: for example, if a patient's an miR-133a level measured by the same methodology is higher than the cut-off value, the patient is deemed to likely respond to oxaliplatin treatment and would therefore be given the treatment; if a patient's miR-133a level is no higher than the cut-off value, the patient is deemed to unlikely respond to oxaliplatin treatment and would therefore not be given the treatment, or would be given the treatment after the patient is first sensitized with miR-133a treatment. In order to provide useful predictions, a cut-off value is chosen such that it would allow predictions to reach at least 70% in both specificity and sensitivity, more preferably at least 75%, 80%, 85%, or higher in both specificity and sensitivity. Typically, the selected group comprises at least 10, 15, 20 or more human colorectal cancer patients.

VI. Combination Treatment of Colon Cancer

By illustrating the correlation of miR-133a amount or level in colon cancer tissue and a patient's likelihood of achieving desirable clinical outcome from conventional chemotherapy regimen such as oxaliplatin administration, especially that increased miR-133a expression can sensitize the patient to achieve improved efficacy of concurrent or subsequent chemotherapy, the present invention provides a novel treatment method for improving therapeutic efficacy among colorectal cancer patients, in particular those who are undergoing chemotherapy such as oxaliplatin treatment. A patient who has been diagnosed with colorectal cancer, for example, at stage IV, may be prescribed to receive chemotherapy in addition to or in lieu of surgical intervention. The patient may, just prior (e.g., 1, 2, 3, 4, 5, 6, or up to 7 days prior) to the start of chemotherapy or at the same time of chemotherapy, receive treatment to temporarily increase the expression level of miR-133a in the colorectal tissue especially colorectal mucosa, such that colorectal cancer cells can be sensitized by miR-133a and become more susceptible to the chemotherapeutic agent such as oxaliplatin, allowing the subsequent or concurrent treatment to yield more favorable clinical outcome.

Patients receiving such pre-treatment or concurrent treatment for increasing miR-133a expression may be measured before, during, and after the miR-133a treatment as well as the anti-cancer chemotherapy to monitor efficacy of the combination therapy regimen. Patients suitable for such combination treatment may include those who inherently have low miR-133a expression level in their colorectal cancer cells and who have been deemed, according the assessment methods of this invention, unlikely to benefit treatment with chemotherapy such as oxaliplatin administration. Once their miR-133a level is higher, especially when reaching a level above the cut-off value, due to the miR-133a treatment, they may become appropriate candidates for the chemotherapy who are likely to achieve desirable clinical outcome and therefore should be given the chemotherapy (such as intravenous oxaliplatin administration).

Various methods can be employed to enhance miR-133a expression, permanently or temporarily. An expression cassette encoding the sequence for miR-133a and capable of directing miR-133a expression may be used for this purpose. Typically, such an expression cassette has a promoter directing the transcription of the miR-133a coding sequence, preferably a tissue-specific promoter directing transcription in the colorectal mucosal tissue, so as to ensure adequate expression of the micro RNA in the colorectal cancer cells. In some embodiments, the expression cassette may be contained within a viral vector or as a part of a virus-like particle that can readily transfect into a target tissue or cell.

An expression cassette for miR-133a expression can be administered directly to the target tissue by injection, e.g., intratumoral injection, or by suppository to the colorectal segment of the digestive tract. One possibility of delivery is via liposomes, which serve to target it to a particular tissue, as well as increase the half-life of the composition. Liposomes include emulsions, foams, micelles, insoluble monolayers, liquid crystals, phospholipid dispersions, lamellar layers and the like. In these preparations the expression cassette to be delivered is incorporated as part of a liposome, alone or in conjunction with a molecule which binds to, e.g., a receptor prevalent among the targeted cells, or with other therapeutic or immunogenic compositions. Formulation for administration by oral, rectal, or other means is contemplated.

VI. Kits

The invention provides compositions and kits for practicing the methods described herein to assess the level of a relevant microRNA (especially miR-133a) in a colorectal cancer sample obtained from in a subject. For example, the miR-133a level is measured in a colon cancer sample taken from a patient, such that the patient may have been treated accordingly, e.g., if the patient is deemed likely to respond positively to oxaliplatin treatment, the patient will be given the treatment; otherwise the patient will not be given oxaliplatin treatment but an alternative treatment, or the patient may be given oxaliplatin treatment only after he is first given miR-133a treatment (for example, administration of an expression cassette such as one contained in a viral vector directing the expression of miR-133a, especially in colorectal tissue including colorectal cancer tissue). In the case of assess likelihood of mortality from colorectal cancer, a patient who has a higher level of miR-133a in his colorectal cancer sample is deemed to have a better chance to survive the disease within the subsequent time period (e.g., 1, 2, 3, 4, 5, or 10 years or 10, 20, 30, 40, or 50 months) than another patient who has a lower level of miR-133a in his colorectal cancer sample.

In some embodiments, kits for carrying out assays for determining miR-133a level typically include reagents useful for carrying out an RT-PCR for the quantitative determination of miR-133a: at least one oligonucleotide useful for reverse transcription and at least one set of three oligonucleotide primers for PCR to amplify the miR-133a sequence. In some cases, one or more of the oligonucleotides may be labeled with a detectable moiety. In some cases, a hydrolysis probe is included in the kit to allow instant quantitative measure of amplification product. Typically, the hydrolysis probe has a fluorescent label and a quencher. Table 1 provides some examples of such primers and probes.

Typically, the kits also include information providing an appropriate cut-off value for the specific assay method. In addition, the kits of this invention may provide instruction manuals to guide users in analyzing test samples and assessing the likelihood of successful oxaliplatin treatment or likelihood of mortality from colon cancer in a test subject.

In a further aspect, the present invention can also be embodied in a device or a system comprising one or more such devices, which is capable of carrying out all or some of the method steps described herein. For instance, in some cases, the device or system performs the following steps upon receiving a colon cancer sample, assessing the likelihood of effective oxaliplatin treatment: (a) determining in the sample the amount or level of a pertinent miRNA species (e.g., miR-133a); (b) comparing the amount/level with a cut-off value or with a second amount/level obtained from a colon cancer sample taken from a second patient; and (c) providing an output indicating whether the patient is likely to benefit from oxaliplatin treatment and therefore should immediately receive such treatment or whether the patient is more likely than the second patient to survive colon cancer with a future time frame (e.g., the next 1, 2, 3, 4, or 5 years, or the next 10, 20, 30, 40, or 50 months). In other cases, the device or system of the invention performs the task of steps (b) and (c), after step (a) has been performed and the amount or concentration from (a) has been entered into the device. Preferably, the device or system is partially or fully automated.

EXAMPLES

The following examples are provided by way of illustration only and not by way of limitation. Those of skill in the art will readily recognize a variety of non-critical parameters that could be changed or modified to yield essentially the same or similar results.

Example: A Novel Predictive Biomarker in Patients with Metastatic Colorectal Cancer Receiving Oxaliplatin-Based Chemotherapy Introduction In this study, the expression hsa-miR-133a-3p is shown to be a useful marker for predicting the response of patients with metastatic colorectal cancer upon receiving oxaliplatin-based chemotherapy and for predicting likelihood of colorectal cancer survival.
Materials and Methods
Human Colorectal Specimens
Tissue Samples A cohort of 42 pairs of tumor and adjacent normal tissue FFPE blocks obtained from stage IV CRC patients who had received oxaliplatin-based treatment as first-line therapy at Prince of Wales Hospital between 2003 and 2010, and with known clinico-oncologic outcomes were identified from the prospectively collected database. Patients were classified into responders and non-responders group according to RECIST guideline (7). Responders are defined as the patients achieving complete response (CR) and partial response (PR), and non-responder group as patients with stable disease (SD) and progressive disease (PD). Overall survival (OS) was calculated from the operation day to the date of death or the last visit with censoring. The progress free survival (PFS) during first-line chemotherapy was determined from the operation day to the first-line progression as documented by either CT scan, positron emission tomography/CT scan, or Carcinoembryonic antigen (CEA). Forty-six mCRC patients received oxaliplatin-based treatment as first-line therapy at Beijing Oncology Hospital were used as a validation cohort (BJ cohort). In addition, fresh snap-frozen (FF) samples with matched FFPE block from another 10 consecutive CRC cases treated on 2004 were randomly selected for testing miRNAs expression correlation. Tissue samples were processed at Department of Anatomical and Cellular Pathology, Prince of Wales Hospital, using the same standard operating procedure over the period they were obtained. CRC tissues and paired adjacent normal tissues were obtained from the resected surgical specimens. The adjacent normal tissue is composed of normal colonic mucosa located at approximately 10 cm away from the cancer tissue. Specimens were immersed in 4% neutral-buffered formalin. The FFPE blocks were stored at room temperature in a standard block storage unit. All subjects provided informed consent prior to specimen collection. The study protocol was approved by the Ethics Committee of The Chinese University of Hong Kong and Beijing Oncology Hospital. This study was carried out in accordance with the Declaration of Helsinki of the World Medical Association.
Cell Lines Cell lines included in the present study (DLD1, HCT116, HT29, RKO, SW1116, HEK293) were obtained from American Type Culture Collection and propagated at 37° C. in the presence of 5% CO2. HCT116p53$^{-/-}$ was a kind gift from Dr. Bert Vogelstein from Ludwig Center at Johns Hopkins. Cell was cultured in Dulbecco's modified Eagle's medium (Thermo Fisher Scientific, Waltham, Mass.) supplemented with 10% (v/v) fetal bovine serum (Thermo Fisher Scientific). All cell lines were obtained between 2013 and 2015 and cell identities were confirmed by short tandem repeat profiling. Routine *Mycoplasma* testing was performed by PCR. Cells were grown for no more than 25 passages in total for any experiment.
miRNA Expression Analysis
Total RNA Isolation Frozen tissue of 20 µg was added into 1 ml Trizol reagent (Thermo Fisher Scientific) in a 1.5 ml tube. The tissue was homogenized by RNase-free pestles and vortexed for 30 seconds to allow for complete homogenization. Total miRNA was extraction was carried out using miRNeasy mini kit (Qiagen, Hilden, Germany) according to the manufacturer's instructions. Total miRNA was eluted in 50 µl nuclease-free water. The RNA concentration was measured with a Nanodrop 2000 spectrophotometer (Thermo Fisher Scientific). Paraffin block was cut into 20 µm sections. 6 sections were used for total RNA isolation with miRNeasy FFPE Kit (Qiagen) according to the manufacturer's instruction. Total RNA was eluted in 50 µl nuclease free water. RNA concentration, ratios of 260/230 and 260/280 were measured by Nanodrop 2000 Spectrophotometer (Thermo Fisher Scientific) (the range of the initial RNA concentration RNA concentration was 200 to 800 ng/µl). All samples were diluted to 40 nanogram per microliter total RNA for further miRNA analysis. 1.2.2 DNA synthesis.
miRNA Reverse Transcription MultiScribe Reverse Transcriptase Kit (Thermo Fisher Scientific) was used to synthesize DNA. The reaction mixture contained 0.6 µL 10× Reverse Transcriptase buffer, 0.06 µL 100 mM dNTP, 0.4 µL 10 µm miR-133a Stem-loop RT primer (SEQ ID NO:1), 0.4 µL reverse transcriptase, 0.076 µL RNase inhibitor and 120 nanogram total RNA in a total of 6 µL reaction mixture. The mixture was incubated at 16° C. for 30 min, then 42° C. for 30 min, then 85° C. 5 min to inactivate the enzymes. The DNA was stored at −80° C. until other application.
miRNA Quantitation by Real-Time Quantitative PCR (qPCR)

qPCR of miR-133a was performed using self-designed miR-133a primer set (Table 1). 100 µM Forward primer, Reverse primer and Hydrolysis probe (SEQ ID NOs:2-4) and H$_2$O were mixed at a ratio of 10:10:3:37 to make a qPCR primer. The qPCR reaction mixture contained 6 µL TaqMan Universal Master Mix II buffer (Applied Biosystems), 0.3 µL miR-133a qPCR primer and 3.3 µL H₂O. qPCR were determined on QuantStudio 7 Flex Real-Time PCR System (Thermo Fisher Scientific). The quantitation of miRNA was based on standard curve (SEQ ID NO:5) plotted by known input amongst all of the miRNA, and normalized to per nanogram of input RNA (8, 9). Assays were performed in a blinded fashion. Cycle threshold (Ct) values >35 were set as the detection limit.

Biological Function Analysis miRNA Transfection

Human miR-133a precursor (PM10413) was purchased from Thermo Fisher Scientific. A control miRNA (miR-Ctrl) (AM17110, Thermo Fisher Scientific) did not target any human genes was used as a negative control. Cells were transfected with miRNAs using Lipofectamine 2000 (Invitrogene). Cells transfected with miRNA were harvested 12 h to 48 h post-transfection.

MTT Cell Viability Assay

After 24 h of transfection, cells were collected and seeded (500-1000/well) in a fresh 96-well plate for 5 days. Cell viability was determined using the conversion of 3-(4,5-dimethylthiazol-2-yl)-2,5-diphenyltetrazolium bromide (MTT) to formazan via mitochondrial oxidation. MTT solution was then added to each well at a final concentration of 0.2 mg/ml per well and the plates were incubated at 37° C. for another 1 h. After incubation, 200 µl of dimethyl sulfoxide was added to each well to dissolve the formazan formed and the absorbance was measured at 570 nm using a spectrophotometer. All the experiments were repeated in three independent experiments in triplicate.

Plasmids and Dual-Luciferase Reporter Assay

Wild-type or mutated human ATP7B, ABCC1 and GCLC 3'-UTR were cloned into pMIR-REPORT vector (Thermo Fisher Scientific) at the SacI and SpeI sites, respectively. Co-transfection of reporter plasmids and miRNA in 24-well plates were carried out with lipofectamine 2000 as described by the manufacture. Per well, 195 ng luciferase report plasmid, 5 ng pRL-cytomegalovirus (CMV) vector and 15 pmole miRNA were applied. Cells were harvested 48 h post-transfection and luciferase activities were analyzed by the dual-luciferase reporter assay system (Promega, Madison, Wis.).

Western Blot Analysis

Protein concentration was measured by the Bradford DC protein assay (Bio-Rad, Hercules, Calif.). 5-20 µg of protein from each sample were separated on 10% Bis-Tris-polyacrylamide gel through electrophoresis and blotted onto nitrocellulose membranes (GE Healthcare, Piscataway, N.J.). Blots were immunostained with primary antibodies at 4° C. overnight and secondary antibody at room temperature for 1 h. Protein was visualized using ECL Plus Western Blotting Detection Reagents (GE Healthcare). Independent experiments were performed at least twice.

Statistics

Differences in miRNA expression between paired lesion tissues and adjacent normal tissues were evaluated by the Wilcoxon matched-pairs test. Receiver operating characteristics (ROC) curves were generated based on the comparison with the control group. Cutoff values were selected using ROC curves for reference, based on a high specificity. The Kaplan-Meier method was used to estimate the PFS during first-line chemotherapy and OS. All reported P values are two-sided, and confidence intervals (CIs) are at the 95% level. P<0.05 was taken as statistically significant. All other statistical tests were performed using Graphpad Prism 5.0 (Graphpad Software Inc., San Diego, Calif.).

Results

Reproducibility of miRNA Detection in Colorectal FFPE Samples

Figure 2B:
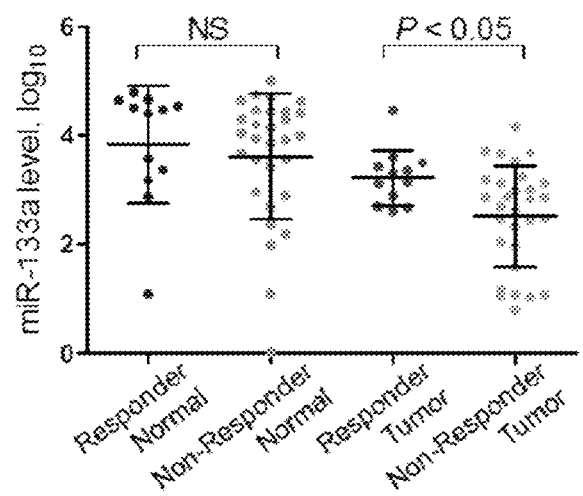
Figure 3A:
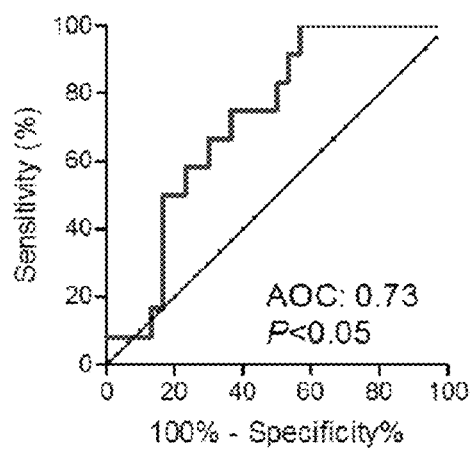
FIGS. 3A-3D: shows patients with low miR-133a expression had significantly poorer OS and PFS in an embodiment.
Figure 3B:
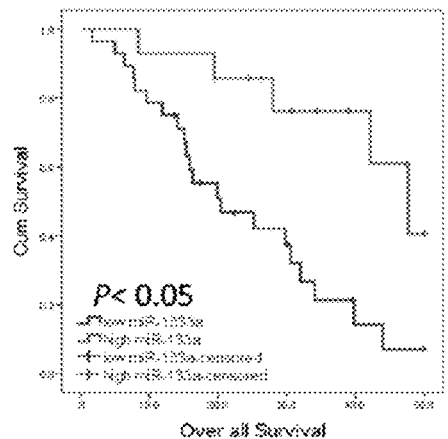
Figure 3C:
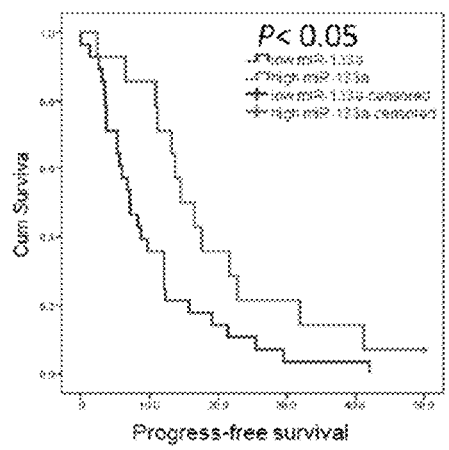

A set of Taqman based real-time PCR primers were first designed for detection of miR-133a (SEQ ID NOs:1-4). In this study, absolute quantification method was used and Ct value was converted to the absolute number of copies/ng RNA based on standard curves obtained from dilution series of known input quantities of synthetic miR-133a (8, 9). A standard curve was created for absolute quantification of miR-133a expression (FIG. 1A). The consistency of miR-133a in CRC FFPE and FF samples was next evaluated. qPCR results indicated that the average Ct value of miR-133a in FFPE sample is 32.3±2.4 compared with the Ct value of 27.9±2.0 from patient-matched FF samples. miR-133a expression in FFPE samples were strongly correlated with that in matched FF pairs (Spearman r=0.88, P<0.001, FIG. 1B), indicating the feasibility of using FFPE samples as replacement for FF samples in miR-133a detection.

miR-133a Expression Levels in Tumor Specimens from Metastatic CRC Patients Associated with their Outcomes to Oxaliplatin Treatment.

miR-133a level was next evaluated in 42 pairs paraffin blocks of tumor and adjacent normal tissues from stage IV CRC patients who had received oxaliplatin-based treatment. Patient median follow-up is 23.4 months (range 1.7-91.9 months). Patients were stratified into responder and non-responder groups according to RECIST guideline. The objective response rate to oxaliplatin regimen is 29% comparable with the response rate (30%-50%) observed in other clinical studies when used as first line therapy (13, 14). In keeping with the previous finding, miR-133a was significantly reduced in tumor FFPE samples compared with adjacent normal counterparts (FIG. 2A, P<0.001). Although miR-133a showed a comparable level in normal tissues of both groups, miR-133a expression was significantly lower in the tumor tissues from non-responder groups compared with those with good response (FIG. 2B, P<0.05). Tumors were further classified into high and low miR-133a expression groups using ROC curve analysis. miR-133a level showed no significant correlation with FFPE block storage period and clinicopathological features such as age, gender, primary cancer site (colon or rectum), metastasis site, oxaliplatin regimen, but was marginally associated with oxaliplatin treatment response (Table 2, P=0.067). The area under the ROC curve (AUC) value for miR-133a was 0.73 for prediction of oxaliplatin treatment outcomes (FIG. 3A). At a cutoff of 1933 copy number per µg input, miR-133a showed a relatively high specificity level (83.33%) and the sensitivity was 50%. Kaplan-Meier survival curves showed that mCRC patients with low miR-133a expression had significantly poorer OS based on the log-rank test (FIG. 3B, P<0.05). Moreover, low miR-133a expression was associated with an increased risk of cancer-related death by univariate Cox regression (Table 3, relative risk (RR) 4.08, 95% CI 1.51 to 11.05, P=0.006). After adjustment for potential confounding factors, low miR-133a level was found to be an independent prognostic factor for shortened overall survival (Table 3, RR 4.18, 95% CI 1.43 to 12.23, P=0.009). Comparison of the miR-133a level with respect to the outcome of first-line PFS revealed that mCRC patients with low miR-133a expression had significantly shorter PFS (FIG. 3C, P<0.05) in Kaplan-Meier survival analysis. Average PFS was 10.4 months in low miR-133a group versus 22.2 months in high miR-133a patients. Low miR-133a expression was associated with an increased risk of shorter progress-free survival by univariate Cox regression (Table 4, RR 2.11, 95% CI 1.09 to 4.12, P=0.029). miR-133a was an independently predictive for PFS during first-line chemotherapy in multivariate Cox regression analysis (Table 4, RR 2.31, 95% CI 1.09 to 4.90, P=0.029).

Figure 3D:
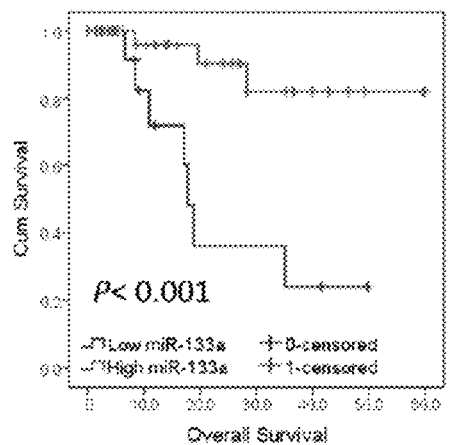

Validation of miR-133a as a Prognosis Biomarker for Overall Survival of mCRC Patients qPCR was performed to validate the prognostic value of miR-133a in an independent research center using BJ cohort of 46 mCRC patients. FF tissue was used in the RNA extraction. Patients were classified into two groups based on the miR-133a level in tumor tissues (Table 5). Upper ⅓ was used as a cut-off (11,312 copy number per μg input, a different cut-off due to the use of a different sample type). Kaplan-Meier survival curves showed that mCRC patients with low miR-133a expression had significantly poorer OS based on the log-rank test (FIG. 3D, P<0.001). Low miR-133a expression was associated with an increased risk of cancer-related death by univariate Cox regression (Table 6, RR 7.33, 95% CI 1.87-28.71, P=0.004). After adjustment for potential confounding factors, low miR-133a level was found to be an independent prognostic factor for shortened OS (Table 6, RR 6.69, 95% CI 1.44-31.16, P=0.015).

Ectopic Expression of miR-133a Sensitizes CRC Cells to Oxaliplatin Treatment

Figure 4:
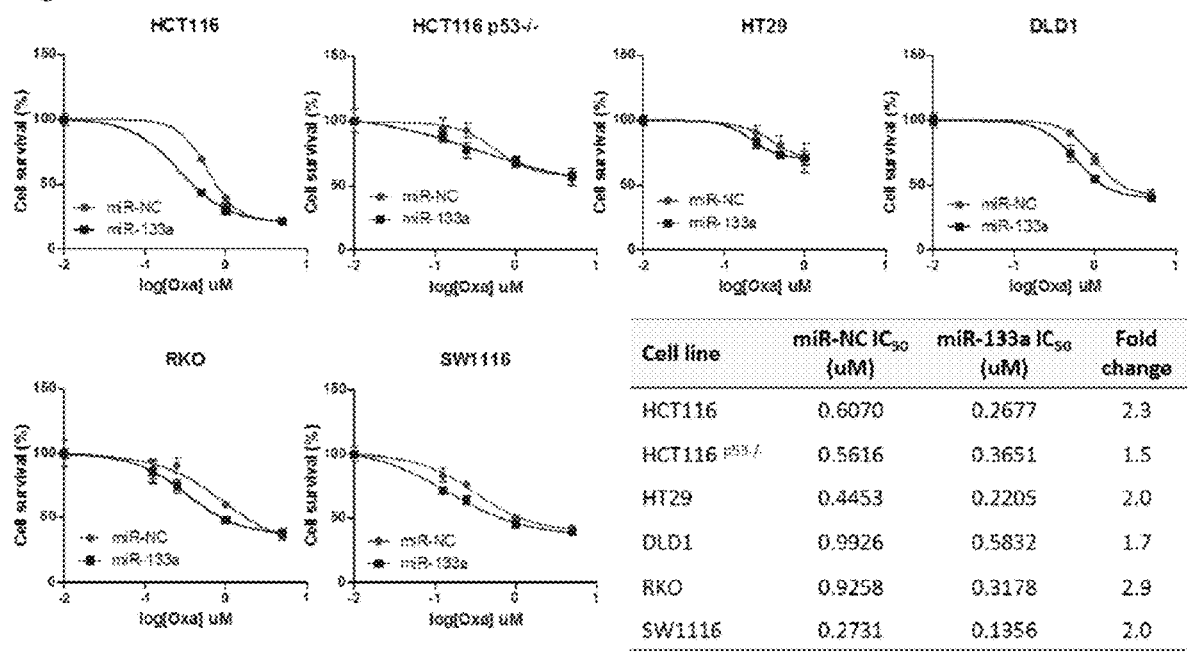
FIG. 4: shows miR-133a sensitizes CRC cells to oxaliplatin treatment in an embodiment. CRC cell lines with ectopic expression of miR-133a showed a lower IC$_{50}$ compared with the control group.

To validate the role of miR-133a in oxaliplatin sensitization in vitro, miR-133a was expressed in the microsatellite stable (HT29, SW1116) and microsatellite instable CRC cell lines (HCT116, HCT116$^{p53-/-}$, RKO, DLD1), respectively. 50% inhibitory concentration ($IC_{50}$) of each cell lines was calculated by means of MTT assay. Restoration of miR-133a was sufficient to result in a 1.5 to 2.9 fold sensitization to oxaliplatin treatment in all the tested cell lines (FIG. 4). Compared with the p53 mutant cell lines, the $IC_{50}$ fold change was more prominent in HCT116 and RKO which have wild-type p53 background, indicating that p53 status is one of the factors that influence the sensitization effect of miR-133a.

miR-133a Sensitizes CRC Cells to Oxaliplatin Treatment Through Suppressing ATP7B, ABCC1, and GCLC To characterize the chemosensitizing property of miR-133a to oxaliplatin treatment, miR-133a targets that regulated the metabolism of oxaliplatin were searched for. Increased drug efflux and activation of detoxification system are two major aspects that induce Platinum-based drugs resistance (15). Previous studies indicate that ATPase Cu++ transporting beta polypeptide (ATP7B), ATP-binding cassette sub-family C member 1 (ABCC1) and γ-glutamylcysteine ligase (GCLC) regulated Platinum-based drugs efflux and detoxification (16-21). Notably, ATP7B, ABCC1 and GCLC contain evolutionarily conserved binding sites for miR-133a. Overexpression of miR-133a significantly suppressed the mRNA of ATP7B, ABCC1 and GCLC in two CRC cell lines HCT116 (p53 wild type) and DLD1 (p53 mutant), indicating that the three genes could also be potential targets that contributing to chemosensitizing property of miR-133a. Furthermore, their predicted 3'UTR binding sites, as well as their mutant form, were attached to firefly luciferase reporter gene, respectively. miR-133a repressed wild-type ATP7B, ABCC1, and GCLC-3'UTR reporter activity for about 64%, 56% and 42%, respectively (FIG. 5A, P<0.05). On the other hand, miR-133a had no inhibition effect on the mutant ATP7B, ABCC1, and GCLC-3'UTR reporter activity, indicting the direct regulation of miR-133a in the 3'UTR of ATP7B, ABCC1, and GCLC mRNA.

To determine whether these finding reflect the regulation of endogenous ATP7B, ABCC1, and GCLC by miR-133a, miR-133a precursor was transiently reintroduced into two colon cancer cell lines HCT116, DLD1 and HEK293 cells. Ectopic expression of miR-133a remarkably reduced ATP7B, ABCC1, and GCLC mRNA and protein expression in the three cell lines (FIGS. 5B and 5C), indicating that they are bona fide targets of miR-133a.

All patents, patent applications, and other publications, including GenBank Accession Numbers, cited in this application are incorporated by reference in the entirety for all purposes.

TABLE 1

DNA sequences of primers used in this study

| Primer Name | Sequence (5'-3') |
|---|---|
| Reverse transcription primer for miR-133a: | |
| Stem-loop RT primer | GTCGTATCCAGTGCAGGGTCC SEQ. ID. NO. 1 GAGGTATTCGCACTGGATACG ACCAGCTG |
| Real-time PCR primers for detection of miR433a expression: | |
| Forward primer | CACGCACTTTGGTCCCCTTCA SEQ. ID. NO. 2 |
| Reverse primer | CCAGTGCAGGGTCCGAGGTA SEQ. ID. NO. 3 |
| Hydrolysis probe | (FAM)TGGATACGACCAGCTG SEQ. ID. NO. 4 G(MGB)(quencher) |
| Homo sapiens mature sequence miR-133a standard | |
| TTTGGTCCCCTTCAACCAGCTG | SEQ. ID. NO. 5 |
| Homo sapiens mature sequence miR-133a | |
| UUUGGUCCCCUUCAACCAGCUG | SEQ. ID. NO. 6 |

Abbreviations:

PCR: RT, reverse transcript; PAM, Fluorescein, a fluorescent dye; MGR, minor groove binder.

TABLE 2

Clinicopathological features and miR-133a expression in 42 colorectal cancer patients

| Variable | miR-133a High (n = 14) | % | miR-133a Low (n = 28) | % | P value |
|---|---|---|---|---|---|
| Age (Mean ± SD) | 63.3 ± 8.6 | | 58.6 ± 12.1 | | 0.053 |
| Gender | | | | | |
| Male | 7 | 53.3% | 12 | 40.7% | 0.748 |
| Female | 7 | 46.7% | 16 | 59.3% | |
| Primary cancer site | | | | | |
| Colon | 13 | 6.7% | 22 | 77.8% | 0.392 |
| Rectum | 1 | 93.3% | 6 | 22.2% | |
| Site of metastasis | | | | | |
| Liver only | 5 | 33.3% | 5 | 18.5% | 0.259 |
| Other organs | 9 | 66.7% | 23 | 81.5% | |
| FFPE storage time | | | | | |
| 2003-2006 | 6 | 40.0% | 11 | 44.4% | 1.000 |
| 2007-2009 | 8 | 60.0% | 17 | 55.6% | |
| Oxaliplatin regimen | | | | | |
| XELOX | 9 | 60.0% | 16 | 59.3% | 0.747 |
| FOLFOX | 5 | 40.0% | 12 | 40.7% | |
| Oxaliplatin response | | | | | |
| Good | 7 | 46.7% | 5 | 14.8% | 0.067 |
| Poor | 7 | 53.3% | 23 | 85.2% | |

TABLE 3

Univariate and multivariate analysis of potential predictive factors of overall survival by a Cox proportional hazards model.

| | Univariate Analysis | | Multivariate Analysis | |
|---|---|---|---|---|
| Variables | RR (95% CI) | P value | RR (95% CI) | P value |
| Age | | | | |
| ≤50 | 0.83 (0.38-1.82) | 0.636 | 0.70 (0.31-1.60) | 0.396 |
| >50 | 1.00 | | 1.00 | |
| Gender | | | | |
| Female | 1.00 (0.45-2.25) | 0.993 | 1.01 (0.44-2.31) | 0.984 |
| Male | 1.00 | | 1.00 | |
| Primary site | | | | |
| Colon | 0.71 (0.27-1.89) | 0.491 | 1.26 (0.44-3.60) | 0.664 |
| Rectum | 1.00 | | 1.00 | |
| Site of metastasis | | | | |
| Liver only | 0.46 (0.69-1.27) | 0.135 | 0.77 (0.26-2.25) | 0.635 |
| Other organ | 1.00 | | 1.00 | |
| miR-133a level | | | | |
| Low | 4.08 (1.51-11.05) | 0.006 | 4.18 (1.43-12.23) | 0.009 |
| High | 1.00 | | 1.00 | |

TABLE 4

Univariate and multivariate analysis of potential predictive factors of progress-free survival by a Cox proportional hazards model.

| | Univariate Analysis | | Multivariate Analysis | |
|---|---|---|---|---|
| Variables | RR (95% CI) | P value | RR (95% CI) | P value |
| Age | | | | |
| ≤50 | 1.14 (0.61-2.13) | 0.685 | 1.02 (0.52-2.03) | 0.950 |
| >50 | 1.00 | | 1.00 | |
| Gender | | | | |
| Female | 1.05 (0.56-1.98) | 0.871 | 1.01 (0.53-1.93) | 0.985 |
| Male | 1.00 | | 1.00 | |
| Primary site | | | | |
| Colon | 0.93 (0.41-2.12) | 0.861 | 1.48 (0.58-3.79) | 0.412 |
| Rectum | 1.00 | | 1.00 | |

TABLE 4-continued

Univariate and multivariate analysis of potential predictive factors of progress-free survival by a Cox proportional hazards model.

| Variables | Univariate Analysis | | Multivariate Analysis | |
|---|---|---|---|---|
| | RR (95% CI) | P value | RR (95% CI) | P value |
| Site of metastasis | | | | |
| Liver only | 0.76 (0.36-1.60) | 0.470 | 0.87 (0.39-1.93) | 0.732 |
| Other organ | 1.00 | | 1.00 | |
| miR-133a level | | | | |
| Low | 2.11 (1.09-4.12) | 0.029 | 2.31 (1.09-4.90) | 0.029 |
| High | 1.00 | | 1.00 | |

TABLE 5

Clinicopathological features and miR-133a expression in 46 mCRC patients from BJ cohort

| Variable | miR-133a High (n = 32) | % | miR-133a Low (n = 14) | % | P value |
|---|---|---|---|---|---|
| Age (Mean ± SD) | 59.3 ± 8.3 | | 55.5 ± 13.5 | | 0.224 |
| Gender | | | | | |
| Male | 21 | 65.6% | 8 | 57.1% | 0.742 |
| Female | 11 | 34.4% | 6 | 42.9% | |
| Primary cancer site | | | | | |
| Colon | 18 | 56.3% | 10 | 71.4% | 0.513 |
| Rectum | 14 | 43.7% | 4 | 28.6% | |
| Site of metastasis | | | | | |
| Liver only | 23 | 71.9% | 11 | 78.6% | 0.729 |
| Other organs | 9 | 28.1% | 3 | 21.4% | |
| Histological type | | | | | |
| Adenocarcinoma | 28 | 87.5% | 13 | 92.9% | 0.423 |
| Mucin-producing adenocarcinoma | 4 | 12.5% | 1 | 7.1% | |
| Oxaliplatin regimen | | | | | |
| XELOX | 24 | 75.0% | 11 | 78.6% | 0.658 |
| Other (FOLFOX/CAPEOX) | 8 | 25.0% | 3 | 21.4% | |
| Differentiation | | | | | |
| Poor | 6 | 18.8% | 3 | 21.4% | 1.000 |
| Well/Moderate | 26 | 81.2% | 11 | 78.6% | |

TABLE 6

Univariate and multivariate analysis of potential predictive factors of overall survival by a Cox proportional hazards model (46 mCRC from BJ cohort).

| Variables | Univariate Analysis | | Multivariate Analysis | |
|---|---|---|---|---|
| | HR (95% CI) | P value | HR (95% CI) | P value |
| Age | | | | |
| ≤60 | 1.13 (0.33-3.91) | 0.85 | 1.30 (0.19-9.12) | 0.79 |
| ≥60 | 1.00 | | 1.00 | |
| Gender | | | | |
| Female | 1.87 (0.54-6.51) | 0.32 | 1.35 (0.22-9.31) | 0.75 |
| Male | 1.00 | | 1.00 | |
| Primary site | | | | |
| Colon | 1.00 (0.28-3.59) | 0.99 | 1.13 (0.27-4.67) | 0.87 |
| Rectum | 1.00 | | 1.00 | |
| Site of metastasis | | | | |
| Liver only | 0.45 (0.12-1.74) | 0.25 | 0.63 (0.11-3.64) | 0.61 |
| Other organ | 1.00 | | 1.00 | |
| Histological type | | | | |
| Adenocarcinoma | 0.63 (0.08-5.15) | 0.67 | 0.55 (0.36-8.54) | 0.67 |
| Mucin-producing adenocarcinoma | 1.00 | | 1.00 | |
| Differentiation | | | | |
| Poor | 2.79 (0.55-14.13) | 0.22 | 1.88 (0.18-19.31) | 0.60 |
| Well/Moderate | 1.00 | | 1.00 | |
| miR-133a level | | | | |
| Low | 7.33 (1.87-28.71) | 0.004 | 6.69 (1.44-31.16) | 0.015 |
| High | 1.00 | | 1.00 | |

LIST OF REFERENCES

1. Torre L A, Bray F, Siegel R L, Ferlay J, Lortet-Tieulent J, Jemal A. Global cancer statistics, 2012. CA: a cancer journal for clinicians. 2015; 65:87-108.

2. Sung J J, Ng S C, Chan F K, Chiu H M, Kim H S, Matsuda T, et al. An updated Asia Pacific Consensus Recommendations on colorectal cancer screening. Gut. 2015; 64:121-32.
3. Xi Y, Nakajima Gavin E, Morris C G; Kudo K, Hayashi K, Ju J. Systematic analysis of microRNA expression of RNA extracted from fresh frozen and formalin-fixed paraffin-embedded samples. RNA. 2007; 13(10):1668-74.
4. Meng W, McElroy J P, Volinia S, Palatini J, Warner S, Ayers L W, Palanichamy K, Chakravarti A, Lautenschlaeger T. Comparison of microRNA deep sequencing of matched formalin-fixed paraffin-embedded and fresh frozen cancer tissues. PLoS One. 2013; 8(5):e64393.
5. Minju Ha and V. Narry Kim. Regulation of microRNA biogenesis. Nature Reviews Molecular Cell Biology volume 15, pages 509-524 (2014)
6. Dong Y, Zhao J, Wu C W, Zhang L, Liu X, Kang W, Leung W W, Zhang N, Chan F K, Sung J J, Ng S S, Yu J. Tumor suppressor functions of miR-133a in colorectal cancer. Mol Cancer Res. 2013 September; 11(9):1051-60. doi: 10.1158/1541-7786.MCR-13-0061.
7. Therasse P, Arbuck S G; Eisenhauer E A, Wanders J, Kaplan R S, Rubinstein L, Verweij J, Van Glabbeke M, van Oosterom A T, Christian M C, Gwyther S G (2000) New guidelines to evaluate the response to treatment in solid tumors. European Organization for Research and Treatment of Cancer, National Cancer Institute of the United States, National Cancer Institute of Canada. J Natl Cancer Inst 92: 205-216
8. Wu C W, Ng S C, Dong Y, Tian L, Ng S S, Leung W W, Law W T, Yau T O, Chan F K, Sung J J, Yu J. Identification of microRNA-135b in stool as a potential noninvasive biomarker for colorectal cancer and adenoma. Clin Cancer Res. 2014 Jun. 1; 20(11):2994-3002. doi: 10.1158/1078-0432. CCR-13-1750.
9. Wu C W, Ng S S, Dong Y J, Ng S C, Leung W W, Lee C W, Wong Y N, Chan F K, Yu J, Sung J J. Detection of miR-92a and miR-21 in stool samples as potential screening biomarkers for colorectal cancer and polyps. Gut. 2012 May; 61(5):739-45. doi: 10.1136/gut.2011.239236.
10. Yujuan Dong, Jun Yu, Simon S M Ng. MicroRNA dysregulation as a prognostic biomarker in colorectal cancer. Cancer Manag Res. 2014; 6: 405-422. doi: 10.2147/CMAR.S35164
11. Dong Y, Wu W K, Wu C W, Sung J J, Yu J, Ng S S. MicroRNA dysregulation in colorectal cancer: a clinical perspective. Br J Cancer. 2011 Mar. 15; 104(6):893-8. doi: 10.1038/bjc.2011.57.
12. Peskoe S B, Barber J R, Zheng Q, Meeker A K, De Marzo A M, Platz E A, Lupold S E. Differential long-term stability of microRNAs and RNU6B snRNA in 12-20 year old archived formalin-fixed paraffin-embedded specimens. BMC Cancer. 2017 Jan. 6; 17(1):32. doi: 10.1186/s12885-016-3008-4.
13. Venook A. Critical evaluation of current treatments in metastatic colorectal cancer. Oncologist. 2005 April; 10(4):250-61.
14. Shields A F, Zalupski M M, Marshall J L, Meropol N J. Treatment of advanced colorectal carcinoma with oxaliplatin and capecitabine: a phase II trial. Cancer. 2004 Feb. 1; 100(3):531-7.
15. Hall M D, Okabe M, Shen D W, Liang X J, Gottesman M M. The role of cellular accumulation in determining sensitivity to platinum-based chemotherapy. Annu Rev Pharmacol Toxicol 2008; 48: 495-535.
16. Miyashita H, Nitta Y, Mori S, Kanzaki A, Nakayama K, Terada K, Sugiyama T, Kawamura H, Sato A, Morikawa H, Motegi K, Takebayashi Y. Expression of copper-transporting P-type adenosine triphosphatase (ATP7B) as a chemoresistance marker in human oral squamous cell carcinoma treated with cisplatin. Oral Oncol 2003; 39: 157-162.
17. Higashimoto M, Kanzaki A, Shimakawa T, Konno S, Naritaka Y, Nitta Y, Mori S, Shirata S, Yoshida A, Terada K, Sugiyama T, Ogawa K, Takebayashi Y. Expression of copper-transporting P-type adenosine triphosphatase in human esophageal carcinoma. Int J Mol Med 2003; 11: 337-41.
18. Ohbu M, Ogawa K, Konno S, Kanzaki A, Terada K, Sugiyama T, Takebayashi Y. Copper-transporting P-type adenosine triphosphatase (ATP7B) is expressed in human gastric carcinoma. Cancer Lett 2003; 189: 33-38.
19. Nakayama K, Miyazaki K, Kanzaki A, Fukumoto M, Takebayashi Y. Expression and cisplatin sensitivity of copper-transporting P-type adenosine triphosphatase (ATP7B) in human solid carcinoma cell lines. Oncol Rep 2001; 8: 1285-1287.
20. Cole S P, Sparks K E, Fraser K, Loe D W, Grant C E, Wilson G M, Deeley R G Pharmacological characterization of multidrug resistant MRP-transfected human tumor cells. Cancer Res 1994; 54: 5902-5910.
21. Godwin A K, Meister A, O'Dwyer P J, Huang C S, Hamilton T C, Anderson M E. High resistance to cisplatin in human ovarian cancer cell lines is associated with marked increase of glutathione synthesis. Proc Natl Acad Sci USA 1992; 89: 3070-3074.

What is claimed is:

1. A method for determining treatment plan in a colorectal cancer patient, comprising the steps of:
   (a) measuring miR-133a level in a colorectal cancer sample taken from the patient;
   (b) comparing the level obtained in step (a) with a cut-off value; and
   (c) determining chemotherapy as likely effective to the patient when the level obtained in step (a) is higher than the cut-off value, and providing to the patient the chemotherapy; or determining chemotherapy as likely ineffective to the patient when the level obtained in step (a) is no higher than the cut-off value, and providing to the patient an alternative treatment different from the chemotherapy,
   wherein the cut-off value is about 1933 copy number per µg input of formalin-fixed paraffin-embedded (FFPE) sample or about 11,312 copy number per µg input of frozen tissue (FF) sample.

2. The method of claim 1, wherein the chemotherapy is oxaliplatin treatment.

3. The method of claim 1, wherein the colorectal cancer patient has at least stage IV colorectal cancer.

4. The method of claim 1, wherein step (a) comprises a polymerase chain reaction (PCR) for measuring the miR-133a level.

5. The method of claim 4, wherein the PCR is a reverse transcription polymerase chain reaction (RT-PCR).

6. The method of claim 5, wherein a primer comprising SEQ ID NO:1, 2, 3, or 4 is used in the RT-PCR.

7. The method of claim 1, further comprising in step (c), when the level obtained in step (a) is no higher than the cut-off value, (i) administering to the patient miR-133a or an expression cassette encoding miR-133a causing increased miR-133a level in the patient's colorectal tissue; and (ii) providing to the patient the chemotherapy.

8. The method of claim 7, wherein the chemotherapy is oxaliplatin treatment.

9. The method of claim 7, wherein the expression cassette is comprised within a viral particle.

10. A method for assessing likelihood of mortality caused by colorectal cancer among colorectal cancer patients, comprising the steps of:
   (a) measuring miR-133a level by reverse transcription polymerase chain reaction (RT-PCR) using a primer comprising SEQ ID NO:1, 2, 3, or 4 in a first colorectal cancer sample taken from a first patient and in a second colorectal cancer sample taken from a second patient;
   (b) determining the miR-133a level in the first sample as being higher than the miR-133a level in the second sample; and
   (c) determining the second patient as having a higher likelihood of mortality caused by colorectal cancer than the first patient.

11. The method of claim 10, wherein each of the first and second patients has stage IV colorectal cancer.

12. The method of claim 10, wherein the likelihood of mortality is for a subsequent time period of about 10, 20, 30, 40, or 50 months.

* * * * *

SEQUENCE LISTING

<160> NUMBER OF SEQ ID NOS: 6

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gtcgtatcca gtgcagggtc cgaggtattc gcactggata cgaccagctg            50

<210> SEQ ID NO 2
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cacgcacttt ggtccccttc a                                              21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccagtgcagg gtccgaggta                                                20

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
tggatacgac cagctgg                                                   17

<210> SEQ ID NO 5
<211> LENGTH: 22
<212> TYPE: DNA
<213> ORGANISM: Homo sapiens

<400> SEQUENCE: 5
tttggtcccc ttcaaccagc tg                                             22

<210> SEQ ID NO 6
<211> LENGTH: 22
<212> TYPE: RNA
<213> ORGANISM: Homo sapiens

<400> SEQUENCE: 6
uuuggucccc uucaaccagc ug                                             22
```